(12) United States Patent
Otsubo

(10) Patent No.: US 6,702,799 B2
(45) Date of Patent: Mar. 9, 2004

(54) DISPOSABLE WEARING ARTICLE

(75) Inventor: Toshifumi Otsubo, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 180 days.

(21) Appl. No.: 09/943,698

(22) Filed: Aug. 31, 2001

(65) Prior Publication Data

US 2002/0029029 A1 Mar. 7, 2002

(30) Foreign Application Priority Data

Sep. 1, 2000 (JP) .......................................... 2000-265506
Apr. 2, 2001 (JP) .......................................... 2001-103962

(51) Int. Cl.[7] ................................................ A61F 13/15
(52) U.S. Cl. ............................. 604/385.21; 604/385.28; 604/385.101
(58) Field of Search .................................. 604/378, 379, 604/380, 385.01, 385.21, 385.23–385.28, 385.101

(56) References Cited

U.S. PATENT DOCUMENTS

| | | | | |
|---|---|---|---|---|
| 5,275,591 A | * | 1/1994 | Mavinkurve | ................. 604/387 |
| 5,382,246 A | | 1/1995 | Kawano | |
| 5,567,265 A | * | 10/1996 | Zajaczkowski | ............. 156/256 |
| 5,624,423 A | * | 4/1997 | Anjur et al. | ............ 604/385.21 |
| 5,643,244 A | * | 7/1997 | Yamaki et al. | ......... 604/385.24 |
| 5,676,661 A | * | 10/1997 | Faulks et al. | ........... 604/385.21 |
| 5,792,130 A | | 8/1998 | Widlund et al. | |
| 5,954,705 A | * | 9/1999 | Sawaki et al. | ........ 604/385.101 |
| 6,056,732 A | * | 5/2000 | Fujioka et al. | .......... 604/385.01 |
| 6,152,907 A | * | 11/2000 | Widlund et al. | ....... 604/385.08 |
| 6,152,908 A | * | 11/2000 | Widlund et al. | ....... 604/385.19 |
| 6,159,191 A | * | 12/2000 | Mishima et al. | ....... 604/385.28 |
| 6,326,525 B1 | * | 12/2001 | Hamajima et al. | .......... 604/378 |
| 6,410,822 B1 | * | 6/2002 | Mizutani | .................... 604/380 |

FOREIGN PATENT DOCUMENTS

| | | |
|---|---|---|
| EP | 1 018 328 A2 | 7/2000 |
| JP | 11-104177 | 4/1999 |
| JP | 11-155904 | 6/1999 |
| JP | 11-299824 | 11/1999 |
| JP | 11-299832 | 11/1999 |

OTHER PUBLICATIONS

Copy of European Search Report dated Dec. 6, 2001.

* cited by examiner

Primary Examiner—Weilun Lo
Assistant Examiner—Catharine L Anderson
(74) Attorney, Agent, or Firm—Butzel Long

(57) ABSTRACT

A disposable wearing article that includes a liquid-absorbent first core disposed between top- and backsheets, a pair of side flaps extending in a longitudinal direction outside transversely opposite side edges of the first core in a crotch region and a pair of second cores spaced from the respective side edges of the first core and disposed between the top- and backsheets. The respective side edges of the first core in the crotch region curve inward in a transverse direction of the article to describe circular arcs while inner side edges of the respective second cores in the crotch region curve outward in the transverse direction of the article to describe circular arcs. The first core and the second cores are bonded together in the vicinity of the side edge portions of the first core and in the vicinity of the inner side edge portions of the second cores in the crotch region so that the side flaps obliquely extend downward from the side edge portions of the first core.

5 Claims, 10 Drawing Sheets

DISPOSABLE WEARING ARTICLE

BACKGROUND OF THE INVENTION

This invention relates to a disposable wearing article adapted to absorb and hold excretion discharged thereon.

Conventional disposable wearing articles comprise a liquid-pervious topsheet lying on body side, a liquid-impervious backsheet lying on side opposed to body side, a liquid-absorbent core disposed between these top- and backsheets and a pair of side flaps extending in a longitudinal direction of the article outside transversely opposite side edges of the core. Such article of open-type is described in Japanese Patent Application Publications Nos. 1999-299824A and 1999-299832A and such article of pants-type is described in Japanese Patent Application Publications Nos. 1999-104177A and 1999-155904A.

Each of these conventional wearing articles is composed, in the longitudinal direction of the article, of a front waist region, a rear waist region and a crotch region extending between these two waist regions wherein a transverse dimension of the core in the crotch region is smaller than that of the core in the front and rear trunk regions so that the core presents an hourglass-like shape in its plan view.

It is well known that, if the transverse dimension of the core in the crotch region is larger than a transverse dimension of a wearer's crotch region, the core will be out of conformity with the wearer's crotch region as the article is put on the wearer's body and the wearer will experience a feeling of incompatibility. To achieve a desired conformity of the core with the wearer's crotch region, the dimension of the core may be adjusted to be equal to or smaller than the dimension of the wearer's crotch region. However, both the wearing articles disclosed in the above-identified Publications are disadvantageous in that an absorption capacity of the core for excretion in the crotch region is deteriorated and a possibility of excretion leak from the crotch region increases as the dimension of the core is reduced.

In most of the wearing articles commercially available, the core is usually dimensioned in the transverse direction to be in a range of 100–200 mm in the crotch region in order to avoid leak of excretion from the crotch region. However, the dimension in such order may often be larger than the dimension of the wearer's crotch region and make it impossible to place the core against the wearer's crotch region with a good conformity.

SUMMARY OF THE INVENTION

It is an object of this invention to provide a disposable wearing article allowing the core lying in the article's crotch region to be placed against the wearer's crotch region with the desired conformity without an anxiety that excretion might leak from the crotch region.

According to this invention, there is provided a disposable wearing article comprising a liquid-pervious topsheet lying on body side, a liquid-impervious backsheet lying not on body side, a liquid-absorbent first core dimensioned larger in a longitudinal direction of the article disposed between the top- and backsheets and a pair of side flaps lying outside transversely opposite edges of the first core and extending in the longitudinal direction so as to configure, in the longitudinal direction, a front waist region, a rear waist region and a crotch region extending between the two waist regions.

According to this invention the side flaps are provided with a pair of second liquid-absorbent cores, each dimensioned to be larger in the longitudinal direction, spaced apart from the respective side edges of the first core outward in the transverse direction by a predetermined dimension, the side edges of the first core extending in the crotch region curve inward in the transverse direction of the article substantially in circular arcs while respective inner side edges of the second cores opposed to the side edges of the first core, respectively, curve outward in the transverse direction of the garment substantially in circular arcs, and in the crotch region, the second cores are drawn toward the first core and the first and second cores are bonded together in the vicinity of the respective side edges of the first core and the respective inner side edges of the second cores so that the side flaps obliquely extend downward from the respective side edges of the first core.

According to one embodiment of this invention, the side flaps are provided with a pair of substantially liquid-impervious leak-barrier cuffs extending in the longitudinal direction of the article and having proximal side edge portions extending along the side edges of the side flaps in the crotch region, free side edge portions being contiguous to the proximal side edge portions and normally biased to rise on the side flaps and longitudinal opposite fixed end portions collapsed inward in the transverse direction and bonded to the side flaps in the front and rear waist regions in such collapsed state and elastic members being stretchable in the longitudinal direction and attached under tension to the free side edge portions.

According to another embodiment of this invention, the minimum transverse dimension of the first core in the crotch region is in a range of 20–80 mm and the maximum transverse dimension of the second core in the crotch region is in a range of 20–70 mm.

According to still another embodiment of this invention, the second core has a stiffness higher than that of the first core.

According to yet another embodiment of this invention, the side flaps are formed with the liquid-pervious topsheet lying on body side and the liquid-impervious backsheet lying on side opposed to body side and the second cores are disposed between these sheets.

DETAILED DESCRIPTION OF THE PREFERRED EMBODIMENTS

Details of the disposable wearing article according to this invention will be more fully understood from the description given hereunder with reference to the accompanying drawings.

Figure 1:
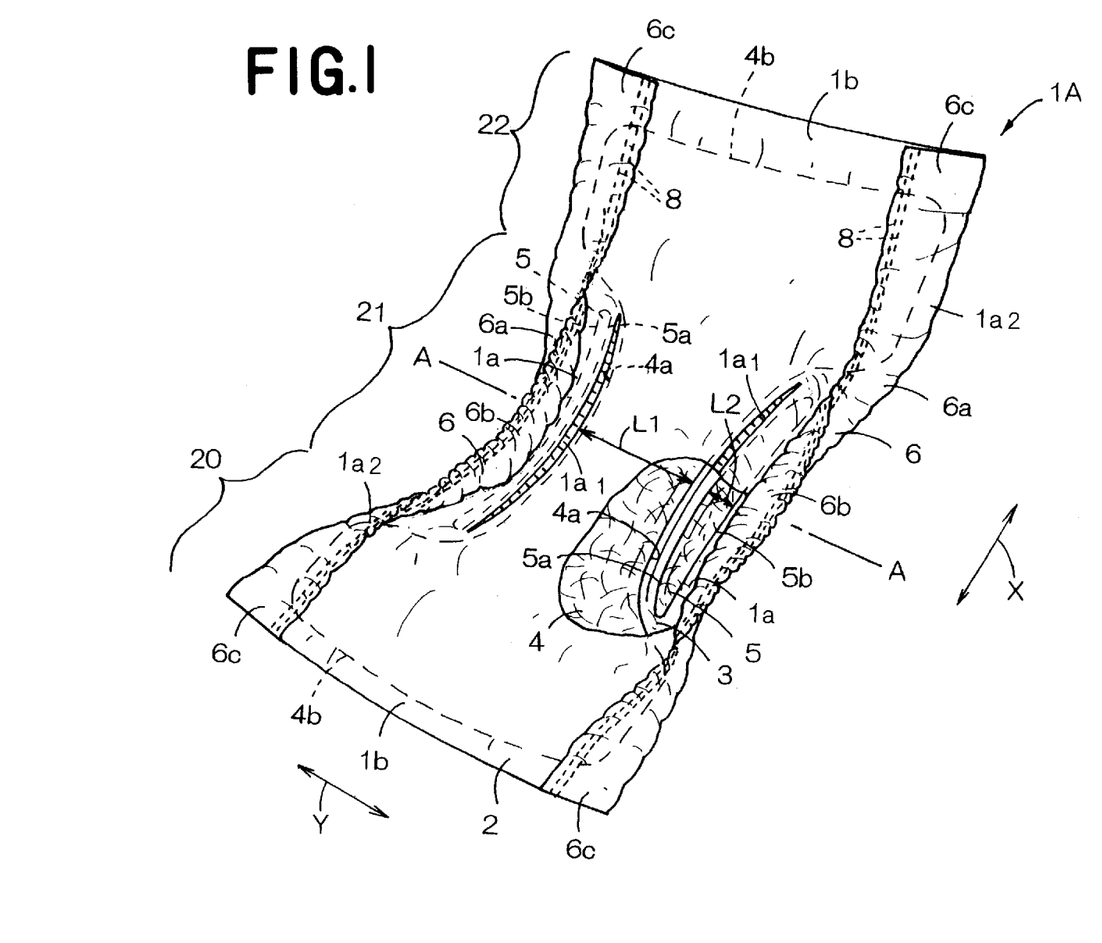
FIG. 1 is a perspective view showing the wearing article of this invention as partially broken away.
Figure 2:
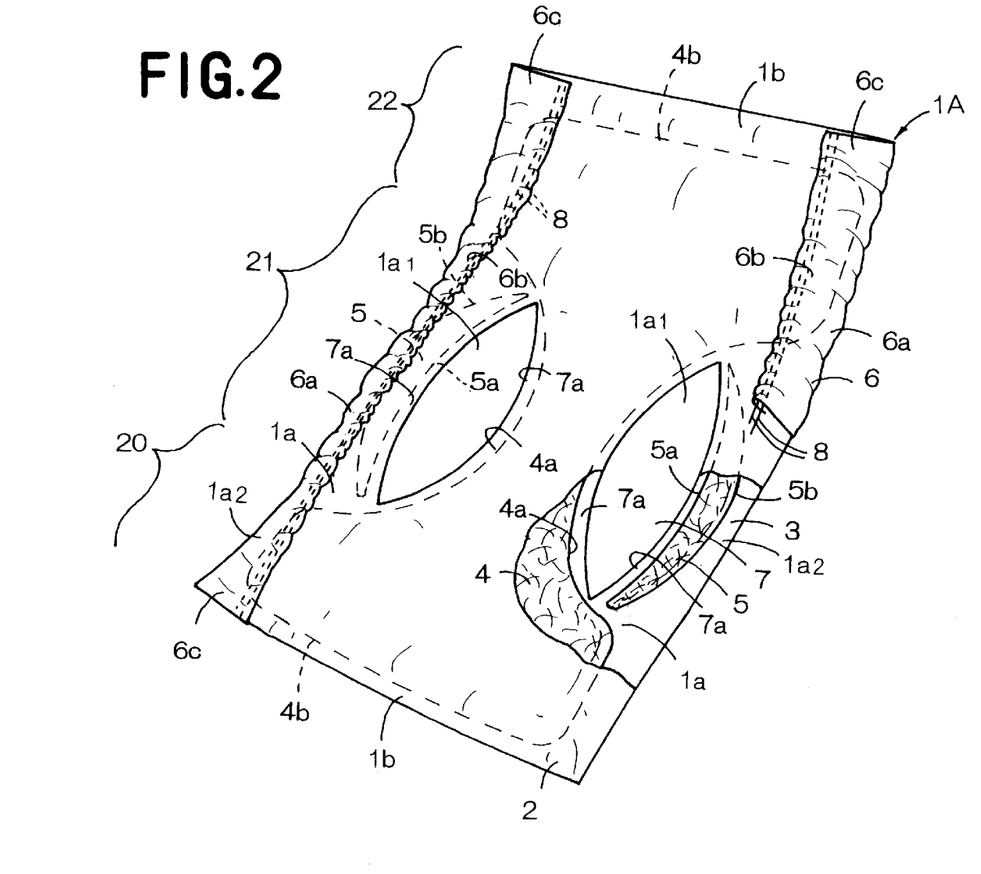
FIG. 2 is a perspective view showing the wearing article as prior to bonding peripheral edges of the openings to close these openings.
Figure 3:
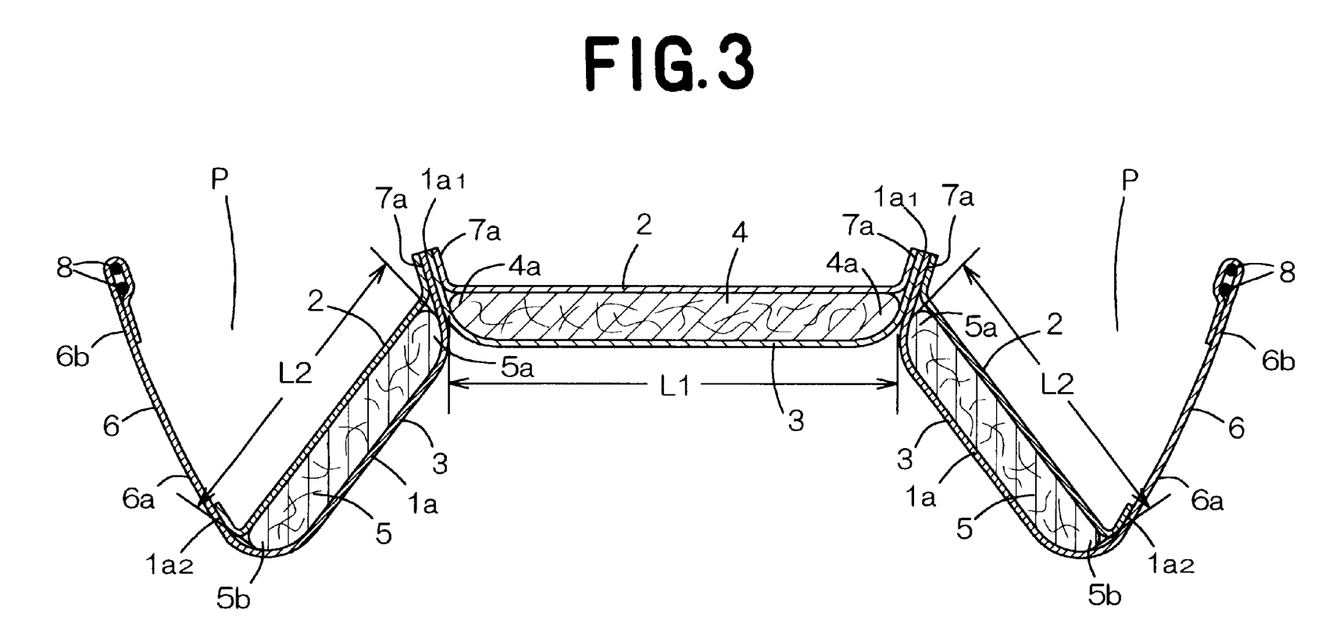
FIG. 3 is a sectional view taken along a line A—A in FIG. 1.

FIG. 1 is a perspective view showing a wearing article 1A as partially broken away, FIG. 2 is a perspective view showing the article 1A as before respective openings 7 have been closed by bonding peripheral edges thereof together, respectively, and FIG. 3 is a sectional view taken along a line A—A in FIG. 1. Referring to FIG. 1, a longitudinal direction is indicated by an arrow X and a transverse direction is indicated by an arrow Y. The herein used expression "inner surfaces" of top- and backsheets 2, 3 should be understood to be the surfaces thereof facing cores 4, 5 and the expression "outer surface" thereof should be understood to be the surfaces thereof being remote from the cores 4, 5.

The article 1A basically comprises a liquid-pervious topsheet 2 lying on a body side, a liquid-impervious backsheet 3 lying on a side opposed to the body side, longitudinally larger first and second liquid-absorbent cores 4, 5 and a pair of substantially liquid-impervious leak-barrier cuffs 6 extending in the longitudinal direction.

Configurationally, the article 1A is composed, in the longitudinal direction, of a front waist region 20, a rear waist region 22, a crotch region 21 extending between said front and rear waist regions 20, 22, a pair of side flaps 1a extending in parallel to each other in the longitudinal direction and a pair of end flaps 1b extending in parallel to each other in the transverse direction.

The first core 4 is disposed between the top- and backsheets 2, 3 and bonded to the inner surface of at least one of the top- and backsheets 2, 3. The first core 4 has transversely opposite side edges 4a extending in the longitudinal direction and longitudinally opposite ends 4b extending in the transverse direction. The side edges 4a of the first core 4 curve inward in the transverse direction of the article 1A substantially in circular arcs in the crotch region 21 (See FIG. 2).

The second cores 5 are respectively provided at the side flaps 1a in the crotch region 21. The second cores 5 are spaced outward in the transverse direction of the respective side edges 4a of the first core 4 by a predetermined dimension and disposed between the top- and backsheets 2, 3 in the respective side flaps 1a and bonded to the inner surface of at least one of these sheets 2, 3. The second cores 5 respectively have inner side edges 5a opposed to the side edges 4a of the first core 4 and extending in the longitudinal direction and outer side edges 5b extending in parallel to the inner side edges 5a in the longitudinal direction. The inner side edges 5a as well as the outer side edges 5b of the second cores 5 curve outward in the transverse direction of the article 1A substantially in circular arcs (See FIG. 2).

The side flaps 1a are formed by portions of the top- and backsheets 2, 3 extending outward in the transverse direction beyond the respective side edges 4a of the first core 4. The end flaps 1b are formed by portions of the top- and backsheets 2, 3 extending outward in the longitudinal direction beyond the longitudinally opposite ends 4b of the first core 4.

In the side flaps 1a, longitudinally larger spindle-shaped zones 1a1 destined to form respective darts are defined between the side edges 4a of the first core 4 and the inner side edges 5a of the second cores 5 are cut off in the vicinity of the transversely opposite side edges 4a of the first core 4 and in the vicinity of the inner side edges 5a of the respective second core 5 to form longitudinally larger spindle-shaped openings 7 as shown in FIG. 2. From the state of the article shown in FIG. 2. Along the peripheral edges 7a of the respective openings 7, the inner surface of the topsheet 2 and the inner surface of the backsheet 3 are bonded together.

Along side edge portions 1a2, the top- and backsheets 2, 3 extend outward in the transverse direction from the respective outer side edges 5b of the second cores 5 and have their inner surfaces bonded together in these extensions.

In the article 1A, the second cores 5 may be drawn from their positions of FIG. 2 toward the first core 4 to close the openings 7 and the peripheral edge portions 7a of the respective openings 7 (the vicinity of the side edges 4a of the first core 4 and the vicinity of the inner side edges 5a of the second cores 5) may be placed upon and bonded to one another to establish the state of FIG. 1.

In the zones 1a1, each pair of the adjacent backsheet sections 3 are put flat together and have their outer surfaces bonded together, as shown in FIG. 3. In the zones 1a1 the peripheral edge portions 7a (the top- and backsheets 2, 3 in the vicinity of the side edges 4a of the first core 4 and in the vicinity of the inner side edges 5a of the second cores 5) of the respective openings 7 extend upward as viewed in FIG. 3. Bonding of the top- and backsheets 2, 3 to each other as well as bonding of the backsheet sections to each other in the zones 1a1 may be carried out using heat-welding technique such as a heat-sealing or an ultrasonic sealing technique.

Configurationally, the article 1A is composed, in the longitudinal direction, of a front waist region 20, a rear waist region 22, a crotch region 21 extending between said front and rear waist regions 20, 22, a pair of side flaps 1a extending in parallel to each other in the longitudinal direction and a pair of end flaps 1b extending in parallel to each other in the transverse direction.

The leak-barrier cuffs 6 have fixed side edge portions 6a lying outside the outer side edges 5b of the second cores 5 and extending in the longitudinal direction along the side edge portions 1a2 of the side flaps 1a in the crotch region 21, free side edge portions 6b being contiguous to the fixed side edge portions 6a and extending in the longitudinal direction and fixed longitudinal opposite end portions 6c lying in the front and rear waist regions 20, 22 and placed upon the topsheet 2.

The fixed longitudinally opposite end portions 6c are collapsed inward in the transverse direction of the article 1A. At these fixed end portions 6c, the inner surface of the backsheet 3 is bonded to the outer surface of the topsheet 2. Longitudinally stretchable elastic members 8 are bonded with tension to the free side edge portions 6b and covered under portions of the free side edge portions 6b.

Referring to FIG. 1, the article 1A curves in the longitudinal direction with the topsheet 2 inside and the free side edge portions 6b of the leak-barrier cuffs 6 rise on the edge portions 1a2 of the side flaps 1a as the elastic members 8 contract. In the crotch region 21 of the article 1A, the side flaps 1a obliquely extend downward from the transversely opposite side edges 4a of the first core 4. With the article 1A worn, the first core 4 is placed against a crotch region of the wearer and the second cores 5 are placed against respective thighs of the wearer.

In the article 1A, the side flaps 1a cooperate with the free side edge portions 6b of the respective leak-barrier cuffs to form a pair of pockets P opening upward of the article 1A so that excretion can be held by these pockets P and thereby a possible leak of excretion from the edge portions 1a2 can be reliably prevented.

The first core 4 preferably has the minimum transverse dimension L1 of 20–80 mm in the crotch region 21. The second cores 5 preferably have the maximum transverse dimension L2 of 20–70 mm, respectively.

In the article 1A, the dimension L1 of the first core 4 is in the range which is smaller than in the article of well known art, so the first core 4 in the crotch region 21 is placed against the wearer's crotch region with a desired conformity without becoming bulky. Even if the article 1A has the first core 4 of a relatively small dimension L1, an amount of excretion possibly leaking from the first core 4 is reliably absorbed by the second cores 5 and it can be avoided that any amount of excretion might leak from the crotch region 21.

If the dimension L1 of the first core 4 is less than 20 mm, an absorbing capacity of the first core 4 for excretion will be remarkably decreased and the amount of excretion absorbed by the first core in the crotch region 21 will be limited and the first core 4 will not be efficiently used. If the dimension L1 of the first core 4 exceeds 80 mm, on the contrary, the dimension L1 of the first core 4 will exceed the transverse dimension of the wearer's crotch region, and the first core 4 will not conform with the wearer's crotch region as the article is worn. With a consequence, the first core 4 will become bulky and will give the wearer a feeling of incompatibility during use of the article.

If the dimension L2 of the second core 5 is less than 20 mm, an absorbing capacity of the second core 5 for excretion will be insufficient to absorb the amount of excretion leaked from the first core 4 and thereby to prevent leak of excretion from the crotch region 21. If the dimension L2 of the second core 5 exceeds 70 mm, on the contrary, the second core 5 will be placed against each of the wearer's thighs over a relatively large extent and constraint a movement of the wearer's legs.

In the article 1A, a stiffness of the second cores 5 is preferably higher than that of the first core 4 in order to ensure that the second cores 5 are prevented from being damaged due to the movement of the wearer's legs transmitted directly to the second cores 5.

Figure 4:
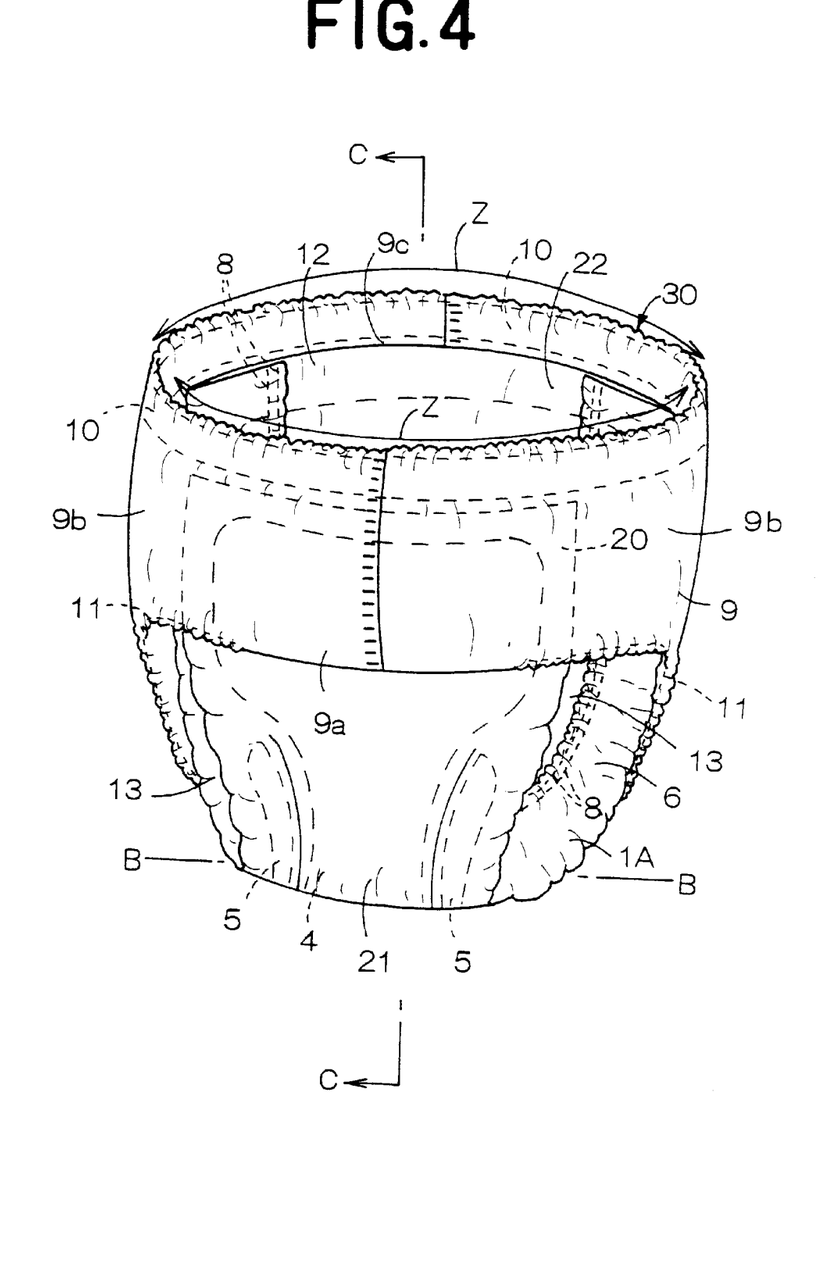
FIG. 4 is a perspective view showing the article of FIG. 1 implemented in the form of a pants-type disposable diaper as partially broken away.
Figure 5:
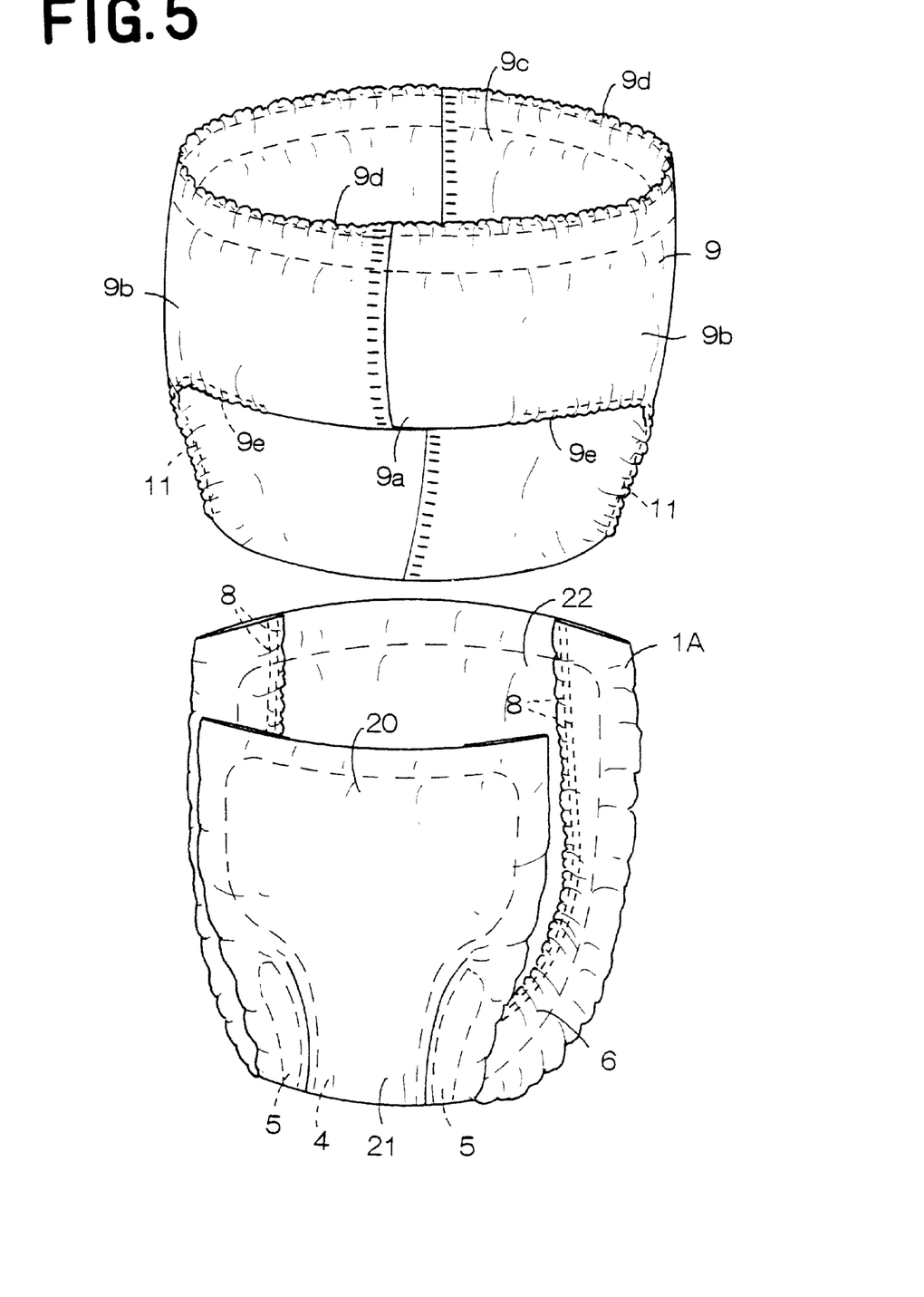
FIG. 5 is a perspective view showing the diaper with the article being separated from the fastening cover member.
Figure 6:
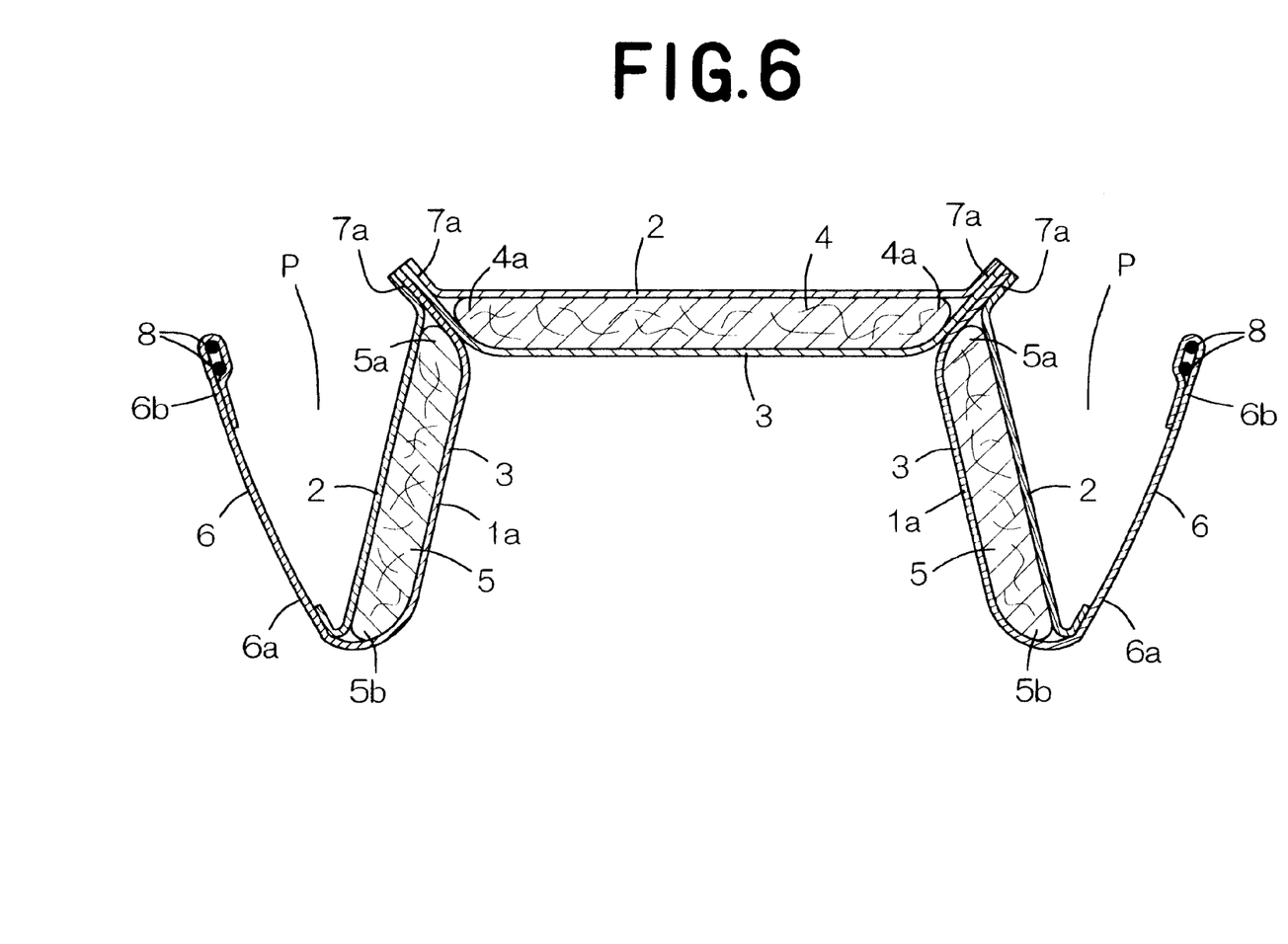
FIG. 6 is a sectional view taken along a line B—B in FIG. 4.
Figure 7:
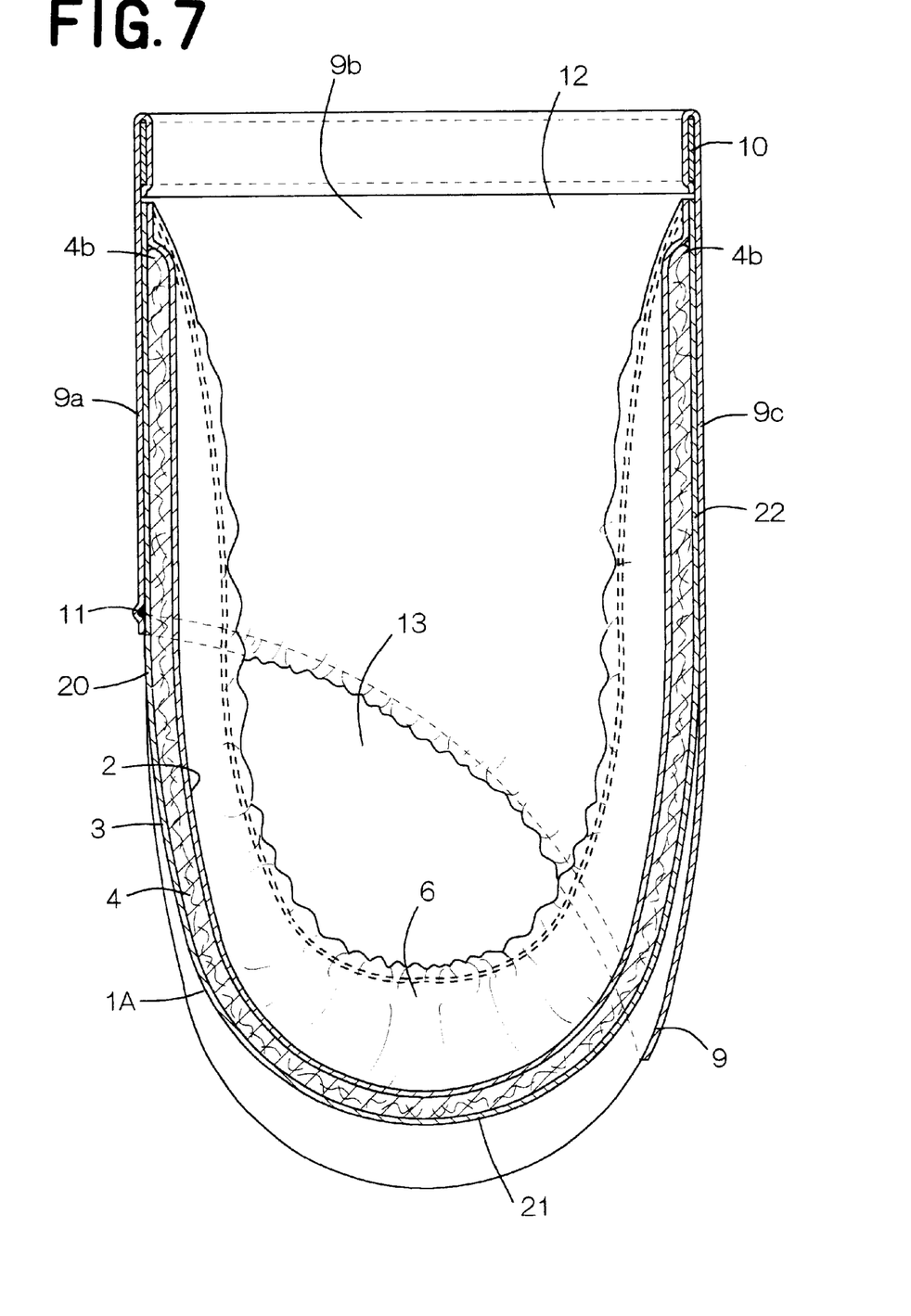
FIG. 7 is a sectional view taken along a line C—C in FIG. 4.

FIG. 4 is a perspective view showing a pants-type disposable diaper 30 using the article 1A of FIG. 1 as partially broken away, FIG. 5 is a perspective view showing this diaper with a fastening cover member 9 being separated from the article 1A, FIG. 6 is a sectional view taken along a line B—B in FIG. 4 and FIG. 7 is a sectional view taken along a line C—C in FIG. 4. Referring to FIG. 4, a waist surrounding direction is indicated by an arrow Z.

The diaper 30 comprises the article 1A and an annular fastening cover member 9. The fastening cover member 9 has a front region 9a to which the front waist region 20 of the article 1A is bonded, a rear region 9c to which the rear waist region 22 of the article 1A is bonded and an intermediate region 9b extending between the front and rear regions 9a, 9c. In the fastening cover member 9, the rear region 9c has an area which is larger than an area of said front and intermediate region 9a, 9b.

An elastic member 10 which is stretchable in the waist surrounding direction is attached under tension to an upper edge portion 9d of the fastening cover member 9 so as to be associated with the waist-opening. Elastic member 11 which is stretchable in the waist surrounding direction is attached under tension to a lower edge portion 9e of the fastening cover member 9. The elastic member 11 extends between the intermediate region 9b and the rear region 9c of the fastening cover member 9. These elastic members 10, 11 are bonded to the fastening cover member 9 by means of hot melt adhesive (not shown).

In the diaper 30, the article 1A is curved in the longitudinal direction with the topsheet 2 inside and the outer surface of the backsheet 3 in the front and rear waist regions 20, 22 of the article 1A is bonded to respective inner surfaces of the front and rear regions 9a, 9b of the fastening cover member 9. The article 1A and the fastening cover member 9 are bonded together by means of hot melt adhesive (not shown). As will be seen in FIG. 4, the article 1A is thus assembled integrally with the fastening cover member 9 so that the crotch region 21 of the article 1A extends downward beyond the fastening cover member 9 and a waist-opening 12 as well as a pair of leg-openings 13 are defined.

With the diaper 30 put on a wearer's body, the fastening cover member 9 is appropriately pressed against the wearer's waist so that the first core 4 of the article 1A may be placed against the wearer's crotch region and the second cores 5 of the article 1A may be placed against the wearer's thighs. In the crotch region 21 of the diaper 30 worn, the side flaps 1a obliquely extend downward from the respective side edges 4a of the first core 4 and cooperate with the free side edge portions 6b of the respective leak-barrier cuffs 6 to define the pockets P opening upwardly of the article 1A, as will be apparent from FIG. 6.

Figure 8:
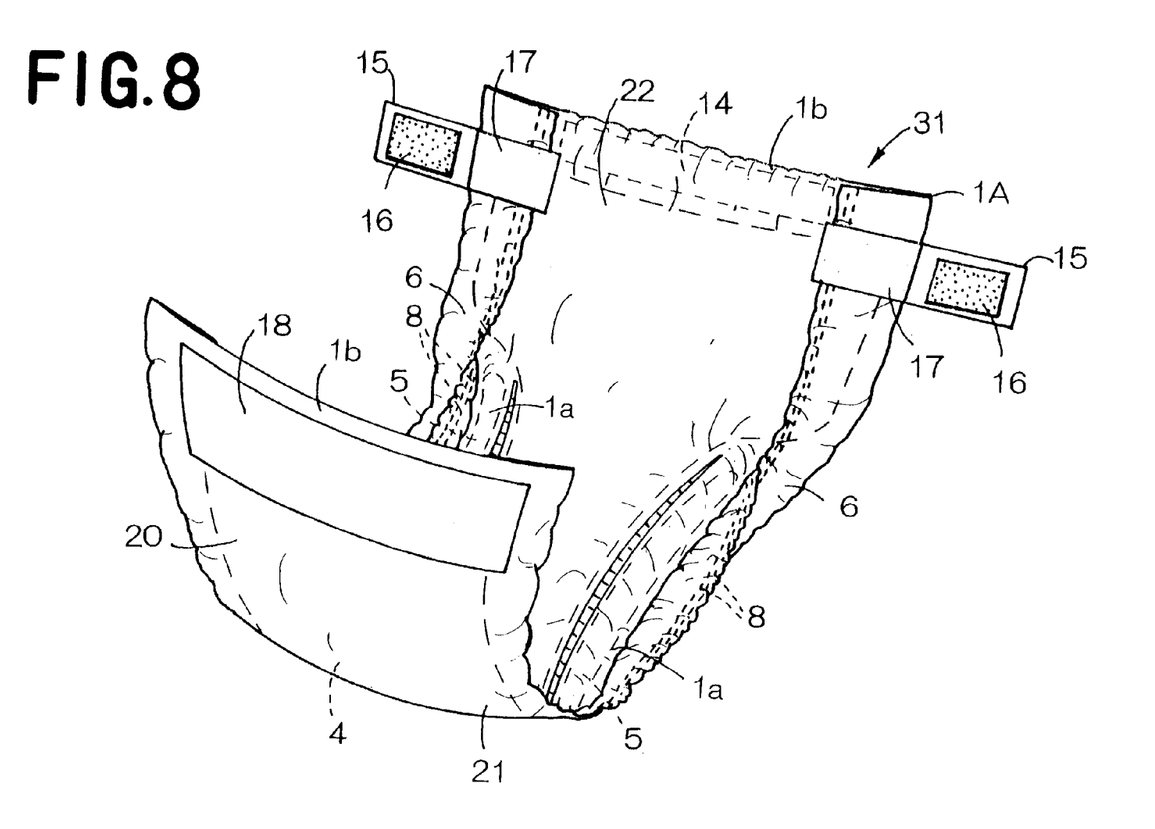
FIG. 8 is a perspective view showing the article implemented in the form of an open-type disposable diaper.

FIG. 8 is a perspective view of the article 1A of this invention implemented in the form of an open-type disposable diaper 31. A ribbon-like elastic member 14 being stretchable in the transverse direction is attached under tension to the end flap 1B in the rear waist region 22 of the article 1A so as to be associated with the waist-opening. This elastic member 14 associated with the waist-opening is disposed between the top- and backsheets 2, 3 in the end flap 1B and bonded to the respective inner surfaces of these sheets 2, 3 by means of hot melt adhesive (not shown).

The side flaps 1a in the rear waist region 22 are provided with a pair of tape fasteners 15, respectively, each extending inward in the transverse direction. Each of these tape fasteners 15 has its proximal end portion disposed between the top- and backsheets 2, 3 and bonded to the respective inner surfaces of these sheets 2, 3 by means of hot melt adhesive (not shown). Each of these tape fasteners 15 has its free end portion coated with pressure-sensitive adhesive 16. Prior to actual use of the diaper 31, the free end portion of the tape fastener 15 remains collapsed toward the outer surface of the topsheet 2 and temporarily, i.e., peelably bonded to plastic film 17 by means of pressure-sensitive adhesive 16 and the film 17 is firmly bonded to the associated leak-barrier cuff 6 in the rear waist region 22. A rectangular target tape strip 18 made of plastic film is firmly bonded to the outer surface of the backsheet 3 in the front waist region 20 by means of hot melt adhesive (not shown). The target tape strip 18 serves as a landing zone on which the tape fasteners 15 are anchored.

With this embodiment of the article 1A, the free end portions of the respective tape fasteners 15 may be anchored on the target tape strip 18 by means of pressure-sensitive adhesive 16 to connect the front and rear waist regions 20, 22 together. Thereupon, the waist-opening (not shown) and the pair of leg-openings (not shown) are defined.

Figure 9:
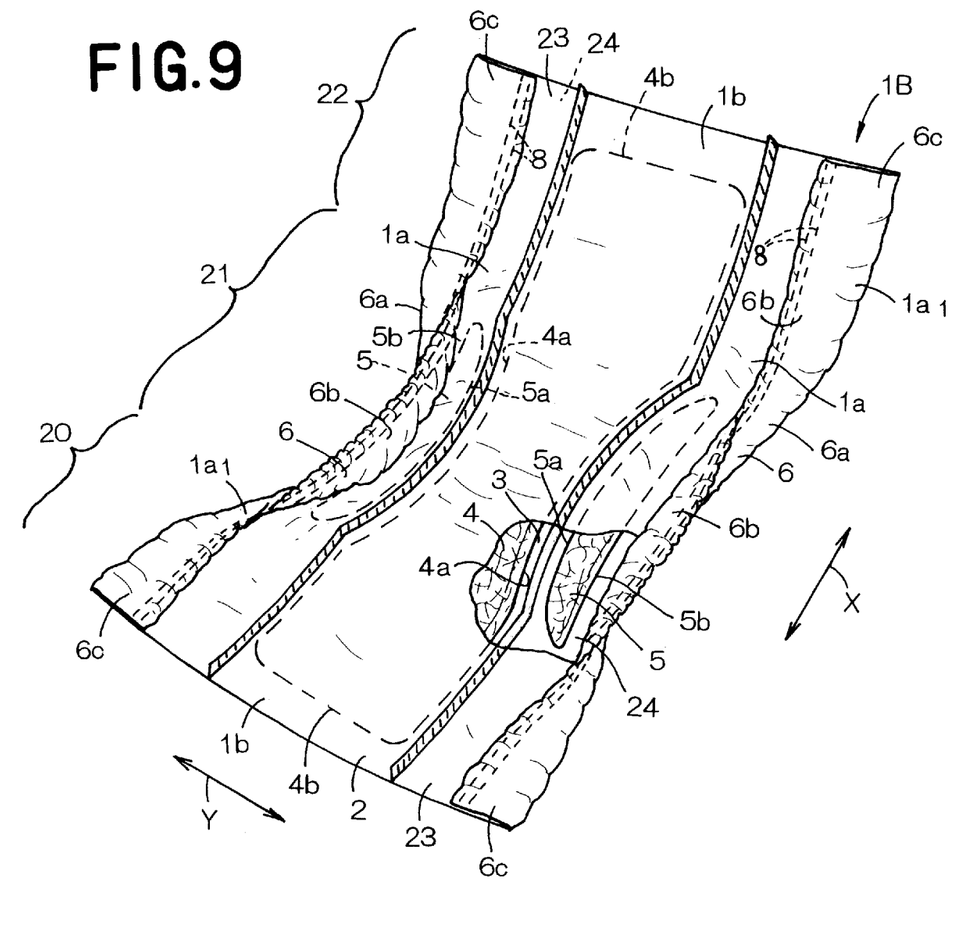
FIG. 9 is a perspective view showing the article implemented in a manner different from the manner in which the article of FIG. 1 is implemented.
Figure 10:
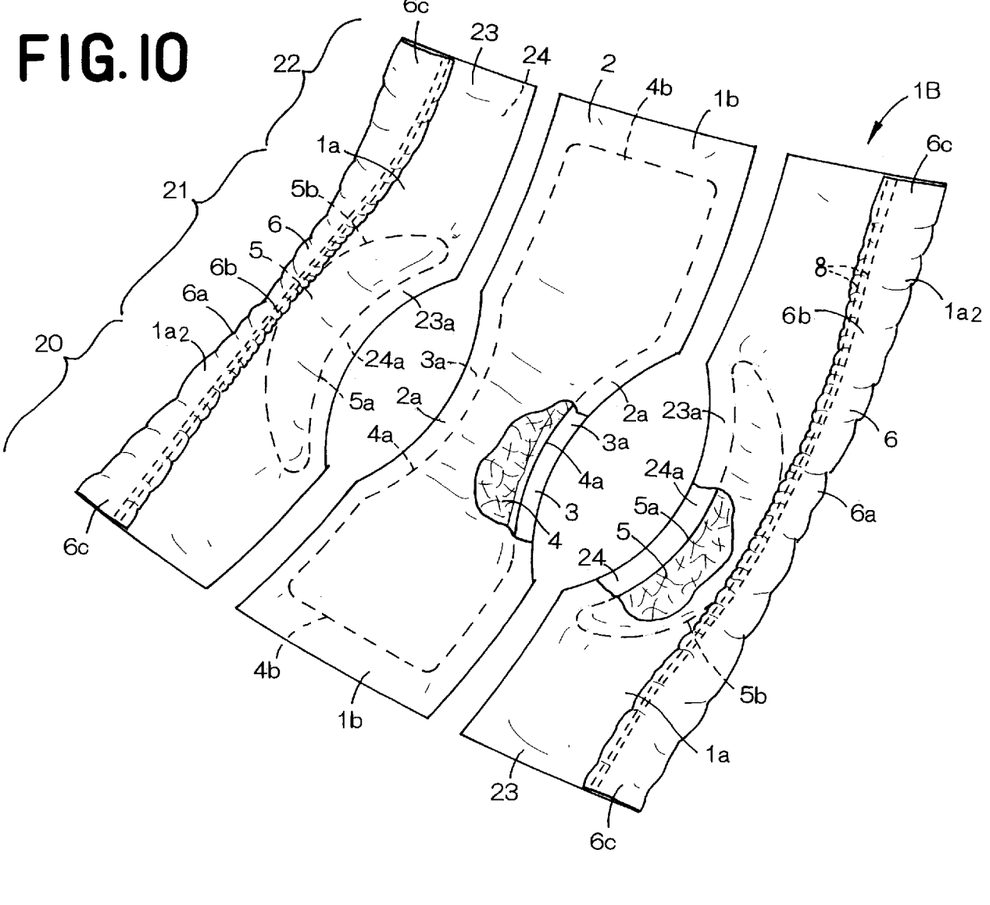
FIG. 10 is an exploded perspective view showing the article of FIG. 9 prior to its assembly as partially broken away.

FIG. 9 is a perspective view showing the article 1B implemented in a manner different from the manner in which the article of FIG. 1 is implemented and FIG. 10 is an exploded perspective view showing the article of FIG. 9 prior to its assembly as partially broken away. Referring to FIG. 9, the longitudinal direction is indicated by an arrow X and the transverse direction is indicated by an arrow Y. The article 1B is different from the article 1A of FIG. 1 in the arrangement as will be described below.

In the case of this article 1B, as will be apparent from FIG. 10, the side flaps 1a are spaced apart from the transversely opposite side edges 4a of the first core 4. The side flaps 1a are formed with a liquid-pervious topsheet 23 lying on body side and a liquid-impervious backsheet 24 lying on side opposed to body side. The second cores 5 are disposed between the top-and backsheets 23, 24 and bonded to the inner surface of at least one of these sheets 23, 24.

Transversely opposite side edge portions 2a, 3a of the top- and backsheets 2, 3 sandwiching the first core 4 and extending outward beyond the side edges 4a of the first core 4 in the transverse direction are put flat together and have their inner surfaces bonded together. In the crotch region 21, the side edges 4a of the first core 4 and the side edge portions 2a, 3a of these sheets 2, 3 curve inward in the transverse direction of the article 1B substantially in circular arcs.

Transversely opposite side edge portions 23a, 24a of top- and backsheets 23, 24 sandwiching the second cores 5 extending inward beyond the inner side edges 5a of the second cores 5 in the transverse direction are put flat together and have their inner surfaces bonded together. In the crotch region 21, the inner side edges 5a of the second cores 5 and the inner side edge portions 23a, 24a of these sheets 23, 24 curve outward in the transverse direction of the article 1B substantially in circular arcs.

In the article 1B, the second cores 5 are drawn toward the first core 4 and the side edge portions 2a, 3a of the sheets 2, 3 are bonded to the inner side edge portions 23a, 24a of the sheets 23, 24. Though not shown, the backsheet sections 3, 24 are put flat together along the side edge portions 2a, 3a and the inner side edge portions 23a, 24a thereof and the outer surfaces of these backsheet sections 3, 24 are bonded to each other.

In the crotch region 21 of the article 1B, the side flaps 1a obliquely extend downward from the side edges 4a of the first core 4. In the article 1B, the side flaps 1a cooperate with the free side edge portions 6b of the leak-barrier cuffs 6 to form a pair of pockets P. With the article 1B put on the wearer's body, the first core 4 is placed against the wearer's crotch region and the second cores 5 are placed against the wearer's thighs.

Similarly to the article 1A of FIG. 4, the article 1B may be combined with the fastening cover member 9 to form the diaper 30. Similarly to the article 1A of FIG. 8, the article 1B may be combined with the tape fasteners 15 and the target tape strip 18 to form the open-type diaper 31. The remaining features of this article 1B are similar to those of the embodiment shown in FIG. 1 and therefore the detailed description of them is not included here.

The topsheets 2, 23 may be formed from a hydrophilic fibrous nonwoven fabric or a plastic film having many fine pores. The backsheet 3, 24 may be formed from a hydrophobic nonwoven fabric, a liquid-impervious plastic film, two-layered hydrophobic fibrous nonwoven fabric or a composite sheet comprising hydrophobic fibrous nonwoven fabric and plastic film bonded to the nonwoven fabric. The cuffs 6 may be formed from hydrophobic fibrous nonwoven fabric. It is also possible to form the backsheets 3, 24 as well as the cuffs 6 from a composite nonwoven fabric comprising highly water-resistant and a flexible melt blown nonwoven fabric and two layers of spun bond nonwoven fabric sandwiching the melt blown nonwoven fabric therebetween.

The nonwoven fabric used for this invention may be of various types such as spun lace-, needle punch-, melt blown-, thermal bond-, spun bond-, chemical bond- and air through-types. The component fiber of the nonwoven fabric may be selected from a group including polyolefine-, polyester- and polyamide-based fibers and core-sheath- type or side-by-side-type polyethylene/polypropylene or polyester conjugated fibers.

The fastening cover member 9 is preferably formed from the stock material similar to that for the backsheets 3, 24 or a stretchable sheet. The stretchable sheet used as the stock material for the fastening cover member 9 may be selected from a group including stretchable and hydrophobic fibrous nonwoven fabric, stretchable and liquid-impervious plastic film, two layered stretchable and hydrophobic fibrous nonwoven fabric and a composite sheet consisting of hydrophobic fibrous nonwoven fabric and liquid-impervious plastic film laminated upon each other and both having a stretchability.

The stretchable fibrous nonwoven fabric may be of melt blown- or spun bond-type. Component fibers of such a stretchable nonwoven fabric may be stretchable fibers obtained by melt-spinning thermoplastic elastomer resin. It is also possible to use a composite nonwoven fabric comprising hydrophobic fibrous nonwoven fabric made of thermoplastic elastomer resin fibers and hydrophobic fibrous nonwoven fabric made of crimped fibers obtained by melt-spinning thermoplastic synthetic resin selected from a group of polypropylene, polyethylene and polyester laminated on at least one surface of the hydrophobic fibrous nonwoven fabric of thermoplastic elastomer resin fibers.

The first and second cores 4, 5 are formed with a mixture of fluff pulp and high absorption polymer grains or a mixture of fluff pulp, high absorption polymer grains and thermoplastic synthetic resin fibers compressed to a desired thickness. Preferably, these cores 4, 5 are entirely covered with tissue paper in order to prevent these cores 4, 5 from getting out of their desired shapes or the polymer grains from falling off from these cores 4, 5. The polymer grains may be selected from a group including starch-based, cellulose-based and synthetic polymer grains. To make the stiffness of the second cores 5 higher than that of the first core 4, for example, a proportion of the thermoplastic synthetic resin fibers in the second cores 5 may be increased and the second cores may be compressed under a relatively high pressure.

Bonding or attachment of the various members such as the top- and backsheets 2, 23, 3, 24, the leak-barrier cuffs 6, the first and second cores 4, 5 and the elastic member 8 may be carried out using suitable adhesive such as hot melt adhesive or heat-welding technique such as heat-sealing or ultrasonic sealing.

The unique construction of the disposable wearing article according to this invention as has been described above allows the transverse minimum dimension of the first core in the crotch region to be smaller than that in the article of well known art. Even if the first core is dimensioned in the direction to be relatively small, an amount of excretion possibly leaking from the first core can be reliably absorbed by the second cores without any anxiety of excretion leakage from the crotch region. In addition, the article according to this invention ensures that the first core in the crotch region well conforms with the wearer's crotch region as the article is worn by the wearer without any feeling of incompatibility.

In the case of the embodiment including the pair of substantially liquid-impervious leak-barrier cuffs extending in the longitudinal direction along the edge portions of the respective side flaps, the free side edge portions of the respective leak-barrier cuffs rise on the edge portions of the side flaps as the elastic members contract. Consequently, the side flaps cooperate with the free side edge portions of the leak-barrier cuffs to form the pockets opening upwardly of the article. In this way, the pockets reliably hold excretion and eliminate an apprehension that excretion might leak from the edge portions of the respective side flaps.

What is claimed is:

1. A disposable wearing article having a body facing side and an opposite side and comprising:
   a liquid-pervious topsheet lying on the body facing side;
   a liquid-impervious backsheet lying on the opposite side;
   a first liquid-absorbent core dimensioned larger in a longitudinal direction than in a transverse direction of the article disposed between said liquid-pervious topsheet and said liquid-impervious backsheet;
   a pair of side flaps laying outside transversely opposite edges of said first liquid-absorbent core and extending in said longitudinal direction;
   a pair of second liquid-absorbent cores provided in said side flaps, each of said second liquid-absorbent cores dimensioned to be larger in said longitudinal direction than in said transverse direction;
   a front waist region;
   a rear waist region;
   a crotch region extending between said front waist region and said rear waist region;
   said side edges of said first liquid-absorbent core which extend in said crotch region curve convexly inward in the transverse direction of said article substantially in circular arcs and respective inner side edges of said second liquid-absorbent cores opposed to said side edges of said first liquid-absorbent core, respectively, curve convexly outward in the transverse direction of said article substantially in circular arcs, in said crotch region, so that a distance measured transversely from the curved inner side edges of the second liquid-absorbent cores to adjacent side edges of the liquid-impervious backsheet is smaller at centers of the second liquid-absorbent cores than at longitudinal ends of the second liquid-absorbent cores and a distance measured transversely across the first liquid-absorbent core between the curved side edges of the first liquid-absorbent core is smaller at a center of the first liquid-absorbent core than at longitudinal ends of the first liquid-absorbent core, said second liquid-absorbent cores are drawn toward said first liquid-absorbent core and said first and second liquid-absorbent cores are bonded together in a vicinity of the respective side edges of said first liquid-absorbent core and the respective inner side edges of said second liquid-absorbent cores so that said side flaps obliquely extend downward from the respective side edges of said first liquid-absorbent core.

2. The wearing article according to claim 1, wherein said side flaps are provided with a pair of substantially liquid-impervious leak-barrier cuffs extending in the longitudinal direction and having proximal side edge portions extending along said side edges of said side flaps in said crotch region, free side edge portions being contiguous to said proximal side edge portions and normally biased to rise on said side flaps, longitudinal opposite fixed end portions collapsed inward in said transverse direction and bonded to said side flaps in said front and rear waist regions in such collapsed state, said elastic members being stretched in said longitudinal direction and attached under tension to said free side edge portions.

3. The wearing article according to claim 1, wherein a minimum transverse dimension of said first liquid-absorbent core in said crotch region is in a range of from about 20 to about 80 mm and a maximum transverse dimension of said second liquid-absorbent cores in said crotch region is in a range of from about 20 to about 70 mm.

4. The wearing article according to claim 1, wherein said second liquid-absorbent cores have a stiffness that is greater than a stiffness of said first liquid-absorbent core.

5. The wearing article according to claim 1, wherein said side flaps are formed from said liquid-pervious topsheet and said liquid-impervious backsheet and said second liquid-absorbent cores are disposed between the liquid-pervious topsheet and the liquid-impervious backsheet.

* * * * *